Figure 1:
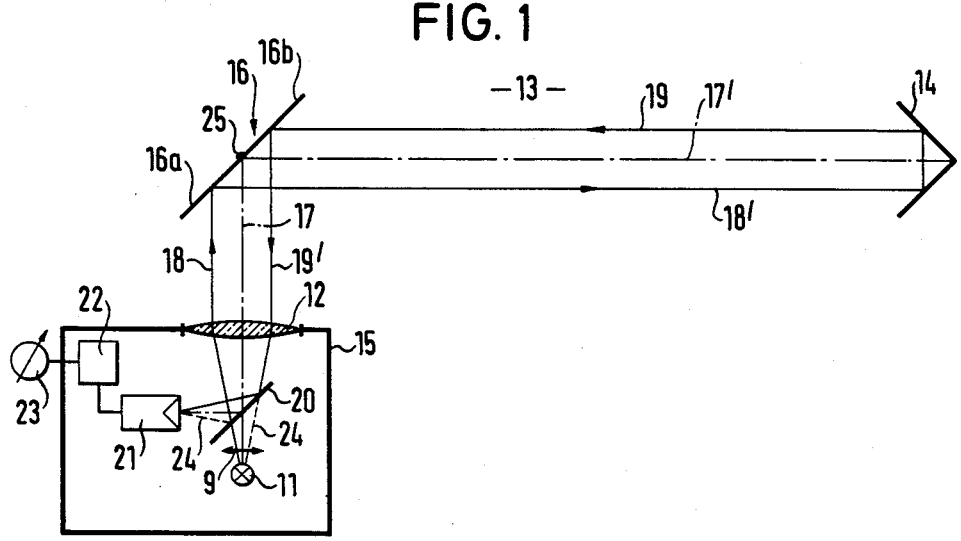

United States Patent [19]

Fetzer et al.

[11] Patent Number: 4,798,965
[45] Date of Patent: Jan. 17, 1989

[54] OPTICAL AUTOCOLLIMATION MEASURING APPARATUS

[75] Inventors: Günter Fetzer, Gundelfingen; Klaus Smetana, Windenreute, both of Fed. Rep. of Germany

[73] Assignee: Erwin Sick GmbH Optik-Elektronik, Waldkirch, Fed. Rep. of Germany

[21] Appl. No.: 65,804

[22] Filed: Jun. 24, 1987

[30] Foreign Application Priority Data

Jan. 18, 1986 [DE] Fed. Rep. of Germany ....... 3624380
Aug. 5, 1986 [DE] Fed. Rep. of Germany ....... 3626524

[51] Int. Cl.$^4$ ............................................. G01N 15/06
[52] U.S. Cl. ..................................... 250/573; 356/436
[58] Field of Search ................... 250/573, 574, 575; 356/436, 437, 438, 439; 350/622

[56] References Cited

U.S. PATENT DOCUMENTS

| | | | |
|---|---|---|---|
| 2,505,505 | 4/1950 | Sachtleber | 350/622 |
| 2,562,181 | 7/1951 | Frommer | 250/574 |
| 3,885,162 | 5/1975 | Geertz | 250/573 |
| 4,001,595 | 1/1977 | Reisman | 250/575 |
| 4,536,091 | 8/1985 | Allington | 250/573 |

*Primary Examiner*—David C. Nelms
*Attorney, Agent, or Firm*—Townsend & Townsend

[57] ABSTRACT

An optical autocollimation measuring apparatus has a light transmitter-receiver arranged in a housing (15). An image of the light source (11) is formed in the objective (12) by a condensor (9) through the beam divider (20). The objective (12) in turn forms an image of the exit pupil of the condensor (9) in the plane of the retroreflector via the measuring path (13). The retroreflector (14) reflects the incident light beam substantially back on itself to the housing (15) of the light transmitter-receiver, where the received light beam is deflected by the beam divider (20) to a photoreceiver (21). A deflecting mirror (16) is located between the front objective (12) and the measuring path (13) and consists of two parts which are pivotable relative to one another, about a pivot axis (25) extending perpendicular to the optical axis (17), from an extended position into a position in which they are displaced by 90° relative to one another. A suitable aperture diaphragm prevents the abutting edges of the two parts of the deflecting mirror being struck by the transmitted light beam.

11 Claims, 3 Drawing Sheets

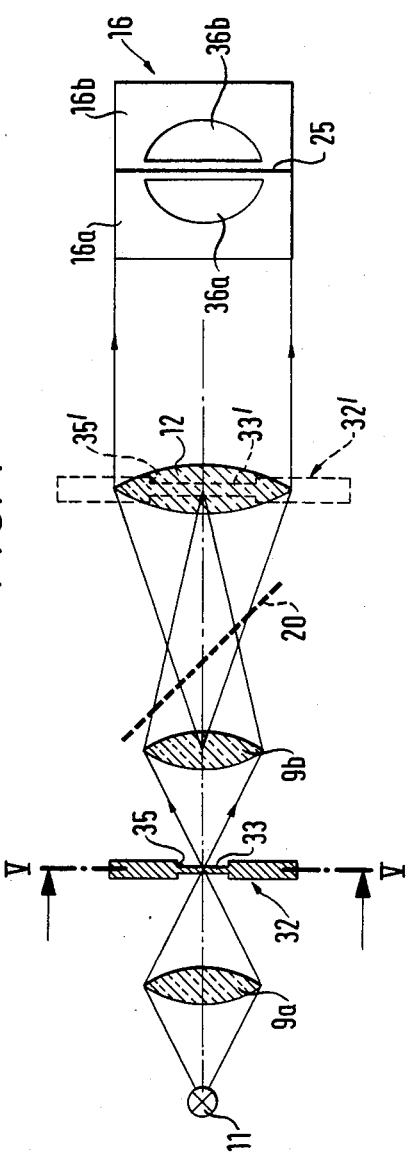
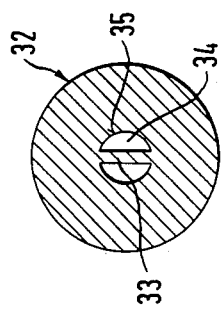
FIG. 4
FIG. 5

OPTICAL AUTOCOLLIMATION MEASURING APPARATUS

The invention relates to an optical autocollimation measuring apparatus comprising a light transmitter-receiver arranged in a housing and having a light source which transmits a light beam via a beam divider and an optical system along a measuring path to a retroreflector, with the retroreflector reflecting the incident light substantially back on itself to the light transmitter-receiver, so that it falls on the beam divider and is deflected from the latter to a photoreceiver, the photoreceiver being connected to an electronic processing circuit which delivers from the electrical output signal of the photoreceiver an indication representative of the optical state along the measuring path. In this apparatus the light source is imaged by a condensor through a beam divider into the objective lens of the light transmitter-receiver. This objective lens in turn forms an image of the exit pupil of the condensor via the measuring path in the plane of the retroreflector.

Autocollimation measuring apparatus of this kind is used by way of example, for visibility or smoke density measuring devices. Such measuring apparatus can also be used for the analysis of the spectral composition of the received light beam in order to determine in this way the proportion of specific gases present along the measuring path. With optical autocollimation measuring apparatus of this kind the problem exists of providing a reference beam path which is stable over long periods of time and independently of the temperature. In order to generate such a reference beam path use has previously been made of optical and electrical components which are not used for the actual measurement along the measuring path. In this way a differential drift of the relevant optical and electrical components can occur, depending on whether they are present in the measurement beam path or in the reference beam path. This differential drift makes itself notable in disadvantageous manner especially with high resolution measuring apparatus.

The principal object underlying the present invention is to provide an autocollimation measuring apparatus of the initially named kind in which at least the important optical and electrical components are the same for both the actual measurement and also the reference measurement, and are used in the same manner, so that eventual drift of specific components over longer periods of time, or changes of temperature, affect the reference measurement and the actual measurement in the same way, and thus do not have any influence on the measurement accuracy.

In order to satisfy this object the invention provides that a deflecting mirror is arranged between front objective and the measuring path and consists of two parts which adjoin one another along a line perpendicular to the optical axis, with the parts being pivotable relative to one another about a pivot axis coincident with the straight line in such a way that on pivoting one part relative to the other part the light impinging on the mirror is retroreflected.

With this arrangement provision should in particular be made for the deflecting mirror to be arranged in the opened up outwardly pivoted state at 45° to the incident light beam, and for the part of the deflecting mirror which is furthest removed from the front objective to be pivotable inwardly through 90° in the direction towards the other fixed part.

Furthermore, it is expedient if both parts of the deflecting mirror are of the same construction.

The deflecting mirror of the invention thus acts during normal measurement as a quite normal continuous plane mirror, since the two parts of the deflecting mirror merge directly into one another during the measurement and lie in one and the same plane. By pivoting one half of the mirror inwardly, in particular through 90°, the measuring path is covered over and the light which is incident on the mirror arrangement, which is now of roof-like form, is retroreflected to the light transmitter receiver. It is important that the deflecting mirror is acted on twice by all light beams during this measurement, in just the same way as during the measurement via the measuring path. Any eventual drift of the deflecting mirror with respect to its degree of reflection in dependence on time and temperature do not play any role during the reference measurement.

In accordance with a first embodiment provision can be made for both parts of the deflecting mirror to each receive one half of the cross-section of the incident outgoing light beam and/or of the retroreflected incoming light beam. In this case the transmitted and received light beams pass through one another.

It is however also possible for one part of the deflecting mirror to receive the incident outgoing light beam and for the other part to symmetrically receive the retroreflected incoming light beam. In this case one half of the aperture is used for light transmission and the other half of the aperture for light reception.

It is particularly expedient for the deflecting mirror to be arranged directly adjacent the objective in front of the measurement path. In this way it is only any eventual changes of the retroreflector over longer periods of time or during temperature changes which affect the measurement, i.e. only changes of a single optical component. All other optical and electronic components are used to the same degree for both the true measurement and also for the referenced measurement.

Migration of the optical axis, which can for example occur due to pivoting of the measuring apparatus, can be compensated for by an embodiment in which the deflecting mirror is mounted on an apparatus by which the angle of the mirror can be changed in two axes. The correcting variable, i.e. the value which is used to effect the correction of the axis is derived from a four-quadrant element which can be blended into the beam path. With this embodiment with an axis follow-up control system it is possible to develop high resolution measuring apparatus, i.e. eventual inhomogeneity of the beam path would not affect the measurement; an under-illumination of the retroreflector would be possible.

A further embodiment is intended to ensure that any disturbances of the reflective capability of the deflecting mirror as a result of its construction from two adjoining parts cannot have disadvantageous effects on the measurement. For this purpose the invention provides that the light source is imaged, preferably in the scale 1:1, onto an aperture diaphragm having a central transverse web, with the aperture diaphragm being imaged in turn preferably into the front objective in such a way that the transverse web keeps back the light which would otherwise fall onto the deflecting mirror in the region of the pivot axis.

The basic thought underlying this further development is thus to be seen in the fact that for the reflection of the measuring light one does not use that region of the foldable deflecting mirror in which the optical reflection characteristics could be disturbed by the abutment of the two edges, i.e. the corresponding part of the measurement light beam is already cut out in the region of the light source. Thus two partial light beams impinge on both sides of the pivot axis on the two parts of the foldable deflecting mirror which have troublefree reflective characteristics.

It is particularly advantageous if the aperture diaphragm has a round circular central opening with the transverse web extending straight across the opening, preferably at the center. With this arrangement provision should in particular be made for the round circular central opening to be imaged into the front objective in such a way that the image of the edge of the central opening has a clear radial spacing from the edge of the front objective.

In this way the entire cross-section of the front objective is not used for the passage of the transmitted light beam but instead only a central part of the front objective. In this way one ensures that certain displacements of the transmitted or received light beam do not result in a change of the optical imaging characteristics. It is important that the circular, round, central opening in the aperture also ensures that the entire cross-section of the foldable deflecting mirror is not used for the reflection of the transmitted light beam. On the contrary a clear spacing should exist at each point of the two parts of the deflecting mirror from the edge of the deflecting mirror up to the incident transmitted light beam.

Figure 2:
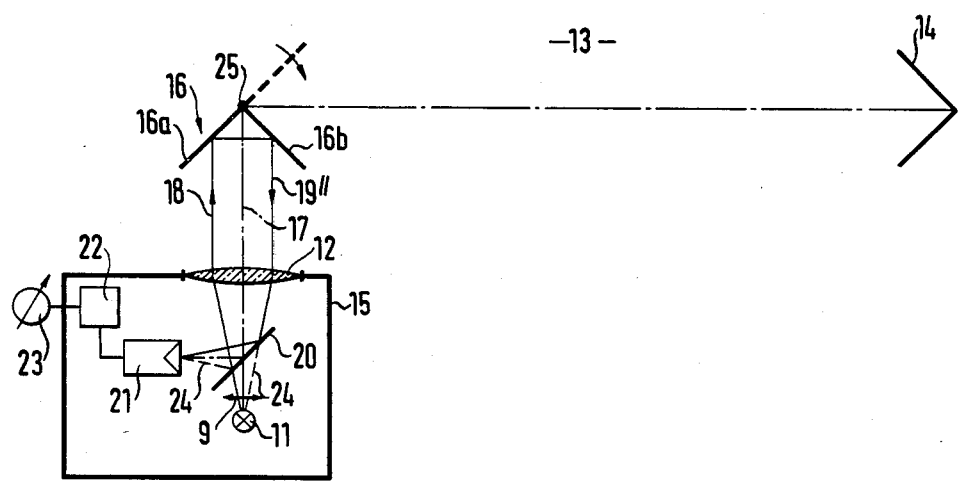
Figure 3:
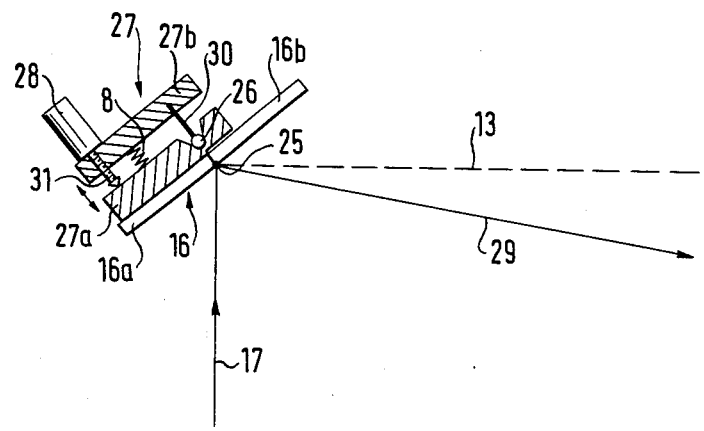
Figure 3A:
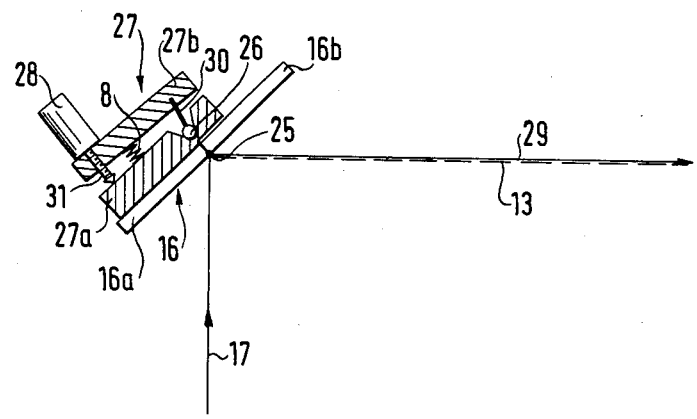

The invention will be described in the following by way of example and with reference to the drawings which show:

FIG. 1 a schematic representation of an autocollimation measuring apparatus in accordance with the invention, and the associated beam path when the deflecting mirror is swung open, FIG. 2 a representation corresponding to FIG. 1 of the same measuring apparatus with the deflecting mirror swung inwardly through 90°, FIGS. 3, 3a a schematic representation of the follow-up control of the optical axis in one plane to an enlarged scale, FIG. 4 a schematic view of the beam path of a further embodiment of the autocollimation measuring apparatus of the invention in the direction perpendicular to the plane of FIG. 1 and seen in the direction of the reflected light beam (19), and FIG. 5 a view of the aperture diaphragm on the line V—V of FIG. 4.

As seen in FIG. 1 a light source 11 with a condensor 9 is arranged in a housing 15. An image of the light source is formed via the condensor lens and a beam divider 20 in a front objective lens 12 provided in the wall of the housing 15. The light source 11 with the condensor 9 is so arranged relative to the front objective 12 that an approximately parallel incident light beam 18 emerges from the front objective 12 which, depending on the construction of the beam divider 20, takes up either only half the whole aperture or the whole aperture (shown in broken lines) of the front objective 12.

A plane deflecting mirror 16 is arranged at a small distance in front of the front objective 12 inclined at 90° to the optical axis 17 of the front objective 12. The plane deflecting mirror deflects the incident light beam 18 through 90° to the measuring path 13 at the end of which a retroreflector 14 is arranged. The retroreflector 14 can be a retroreflector consisting of numerous triples, a single triple prism or also a Beck prism. In the latter case the light beams extending to one side of the optical axis 17' would be symmetrically displaced by the reflector 14 to the other side of the optical axis 17' and return from there back to the deflecting mirror 16 parallel to the incident beam. In this way a reflected beam 19 would be created which extends parallel to the incident light beam 18' and which finally re-enters the interior of the housing 15 through the front objective 12 as the retroreflected and reflected beam 19', and would then be reflected by the beam divider 20 sideways to a photoreceiver 21. The photoreceiver 21 is connected to an electronic processing circuit 22 which delivers from the output signal of the photoreceiver 21 an indication representative of the optical state at or along the measurement path 13.

In accordance with the invention the plane deflecting mirror 16 is subdivided into two identical halves 16a, 16b which abut against one another on the optical axis 17, 17' along a line which extends perpendicular thereto. The two parts 16a, 16b of the deflecting mirror 16 are connected with one another by a pivot axle 25 precisely along this straight line of contact. Whereas the part 16a of the deflecting mirror 16 is fixedly arranged, the part 16b of the deflecting mirror can be pivoted downwardly from the position shown in FIG. 1 (shown in broken lines in FIG. 2) in the direction of the arrow in FIG. 2 into a position displaced by 90°. In this position the two parts 16a, 16b of the deflecting mirror 16 are arranged at an angle of 90° to one another in such a way that the incident light beam 18 is reflected from the part 16a through 90° to the part 16b and is finally reflected from the latter back to the front objective 12 as a reference reflection beam 19".

In the manner indicated in broken lines in FIGS. 1 and 2 the incident and received light beams could however also extend over both halves of the aperture of the front objective 12. In this case the part of the incident light beam 18 which extends on one side of the optical axis 17 would be displaced in parallel to itself onto the other side of the optical axis 17 and vice versa. In the outwardly pivoted position of the part 16b of the deflecting mirror 16 of FIG. 1, the deflecting mirror 16 acts as a normal plane mirror. However, in the inwardly pivoted position of FIG. 2 in which it is pivoted through 90° the deflecting mirror 16 is converted into a roof-shaped mirror, representing a one dimensional retroreflector. In this position all light incident at any position at 45° on the two parts 16a, 16b is displaced parallel to itself and is again reflected back to the front objective 12, and indeed in the same manner as takes place at the retroreflector 14 at the end of the measurement path 13 when the latter is a single roof edge prism or a single triple mirror such as a Beck prism.

In this way it is ensured that both during the actual measurement of FIG. 1 and during the reference measurement of FIG. 2 all electrical and optical components, with the exception of the retroreflector 14 at the end of the measurement path, are used in the same manner for both measurements.

In accordance with FIG. 3 the deflecting mirror 16 with its parts 16a, 16b can be mounted on a device 27 which consists of two plates 27a, 27b of which the one (27a) is secured to the rear side of the mirror 16. The other plate 27b is arranged at a small distance behind it and is connected at the level of the pivot axle 25 by a link 30 with a pivot point 26, for example a ball joint, arranged in the plate 27a at the level of the pivot axis 25.

In the opposite end region the two plates 27a, 27b are connected to one another via a positioning member 31 of variable length, the length of which can be adjusted by an adjusting mechanism 28, for example a micrometer screw.

The plate 27b and the micrometer screw 28 are fixedly arranged on the housing. In this way an adjustment of the micrometer screw 28 can change the spacing of the two plates 27a, 27b at one side, while the spacing remains substantially constant in the region of the ball joint 26. The plates 27a, 27b are biased towards one another by a spring 8.

As a result of this construction a light beam which is deflected away from the correct direction along the measuring path 13, for example by pivoting of the housing, can be corrected by enlarging the spacing of the two plates 27a, 27b by making the positioning member 31 (FIG. 3a) longer. In other words the light beam 29 can be pivoted so that it extends in the desired direction over the measuring path. In this way it is straightforwardly possible to compensate for faulty alignment of the measuring light beam in an angular range of ca. 5°.

The possibility of follow-up control of the axis also likewise makes under-illumination of the retroreflector possible.

In FIGS. 4 and 5 the same reference numerals designate parts which have counterparts in the preceding embodiments.

As seen in FIG. 4 an image of the light source 11 is formed via a first lens 9a in a circular aperture diaphragm 32, there being a vertical transverse web 33 which extends across this aperture diaphragm. Radially outwardly the diaphragm 32 extends sufficiently far that all light which is incident outside of the round circular central opening 34 is absorbed.

A lens 9b arranged behind the aperture diaphragm 32 images the aperture diaphragm 32 to an enlarged scale in the front objective 12, i.e. an image 32' of the aperture diaphragm 32 is present in the front objective 12. The image 33' of the transverse web 33 thus likewise lies centrally in the objective 12.

The radius of the edge 35 of the circular opening 34 is so small that the image 35' of the edge 35 is located at a substantial distance radially inwardly from the periphery of the front objective 12.

The transverse web 33, or its image 33', is so arranged that the parallel light beam emerging from the front objective 12 has a blanked out region at the center which lies on the surface of the deflecting mirror 16 in the region of the pivot axle 25 and extends away from the pivot axle 25, or from the abutting edges of the two parts 16a, 16b by a certain amount in opposite directions. In this way the region of the deflecting mirror 16 surrounding the abutting edges of the parts 16a, 16b is excluded from the reflection of the measuring light beam.

Moreover, the edge 35 of the central opening 34 is so disposed that the two partial light beams 36a, 36b not only do not contact the abutting edges of the two parts 16a, 16b of the deflecting mirror 16 but moreover also do not extend up to one of the edges of the deflecting mirror 16. In this way certain tolerances are possible in the constructional arrangement of the deflecting mirror 16.

We claim:

1. Optical autocollimation measuring apparatus, in particular transmission measuring apparatus, comprising a light transmitter-receiver arranged in a housing and having a light source which transmits a light beam via a beam divider and an optical system over a measurement path to a retroreflector with the retroreflector reflecting the incident light substantially back on itself to the light transmitter-receiver so that it falls on the beam divider and is deflected by the latter to a photoreceiver to which an electronic processing circuit is connected, which delivers from the electrical output signal of the photoreceiver an indication representative of the optical state along the measurement path, characterised in that a deflecting mirror (16) is arranged between the front objective (12) and the measurement path (13) and consists of two parts (16a, 16b) which adjoin one another along a straight line standing perpendicular to the optical axis (17), with the parts being pivotable relative to one another about a pivot axis coinciding with the straight line in such a way that by rotating one part (16b) relative to the other part (16a) the light incident on the mirror is retroreflected in one dimension.

2. Measuring apparatus in accordance with claim 1, characterised in that the deflecting mirror (16) is arranged in the uncovered state at 45° to the incident light beam (18) and in that the part (16b) of the deflecting mirror (16) which is furthest removed from the front objective (12) can be pivoted inwardly through 90° in the direction towards the other stationary part (16a).

3. Measuring apparatus in accordance with claim 1, characterised in that both parts of the deflecting mirror (16) are of the same construction.

4. Measuring apparatus in accordance with claim 1, characterised in that both parts (16a, 16b) of the deflecting mirror (16) each receive one half of the cross-section of the incident outgoing light beam (18) and/or of the reflected incoming light beam.

5. Measuring apparatus in accordance with claim 1, characterised in that the deflecting mirror is arranged outside of the housing (15) directly adjoining the measuring path (13).

6. Measuring apparatus in accordance with claim 1, characterised in that the deflecting mirror (16) is mounted on a device (27) which makes it possible to compensate for migration of the optical axis relative to the reflector, for example by tilting the apparatus.

7. Measuring apparatus in accordance with claim 1, characterised in that the light source (11) is preferably imaged in the scale 1:1 onto an aperture diaphragm or stop (32) having a central transverse web (33) which is in turn imaged in such a way, preferably into the front objective (12), that the transverse web (33) holds back the light which would otherwise fall onto the deflecting mirror (16) in the region of the pivot axis (25).

8. Measuring apparatus in accordance with claim 7, characterised in that the aperture stop (32) has a round circular central opening (34) across which the transverse web (33) extends, preferably at the center.

9. Measuring apparatus in accordance with claim 8, characterised in that the round circular central opening (34) is imaged into the front objective (12) in such a way that the image (35') of the edge (35) of the central opening (34) has clear radial spacing from the edge of the front objective (12).

10. Optical autocollimation measuring apparatus, in particular transmission measuring apparatus, comprising a light transmitter-receiver arranged in a housing and having a light source which transmits a light beam via a beam divider and an optical system over a measurement path to a retroreflector with the retroreflector reflecting the incident light displaced parallel to itself to the light transmitter-receiver so that it falls on the beam divider and is deflected by the latter to a photoreceiver to which an electronic processing circuit is connected, which delivers from the electrical output signal of the photoreceiver an indication representative of the optical state along the measurement path, characterised in that a deflecting mirror (16) is arranged between the front objective (12) and the measurement path (13) and consists of two parts (16a, 16b) which adjoin one another along a straight line standing perpendicular to the optical axis (17), with the parts being pivotable relative to one another about a pivot axis coinciding with the straight line in such a way that by rotating one part (16b) relative to the other part (16a) the light incident on the mirror is retroreflected in one dimension.

11. Measuring apparatus in accordance with claim 10, characterised in that one part (16a) of the deflecting mirror (16) receives the outgoing light (18), while the other part (16b) symmetrically receives the incoming reflected beam (19).

* * * * *